United States Patent [19]
Ebling et al.

[11] 3,979,665
[45] Sept. 7, 1976

[54] CONDUCTIVITY MONITORING SYSTEM

[75] Inventors: Wendell V. Ebling, Libertyville, Ill.;
Herbert Goldsmith, Rockville;
Rodolfo R. Rodriquez, Columbia,
both of Md.

[73] Assignee: Baxter Laboratories, Inc., Deerfield, Ill.

[22] Filed: Feb. 5, 1975

[21] Appl. No.: 547,319

[52] U.S. Cl. ............................ 324/30 R; 324/30 B;
204/195 R
[51] Int. Cl.² ........................................ G01N 27/42
[58] Field of Search ....................... 324/30 B, 30 R;
204/195 R

[56] References Cited
UNITED STATES PATENTS

| | | |
|---|---|---|
| 3,086,169 | 4/1963 | Egnon ............................. 324/30 B |
| 3,493,857 | 2/1970 | Silverman ......................... 324/30 B |
| 3,549,989 | 12/1970 | Brown ............................. 324/30 B |
| 3,582,767 | 6/1971 | Brum ............................. 324/30 B |

*Primary Examiner*—R. V. Rolinec
*Assistant Examiner*—Michael J. Tokar
*Attorney, Agent, or Firm*—Robert E. Knechtel; Richard G. Kinney

[57] ABSTRACT

A conductivity monitoring system including a temperature sensing means for sensing the temperature of a fluid and also providing a temperature compensated conductivity signal. Electronic circuitry is provided for detecting and indicating the inoperability of the temperature sensor.

2 Claims, 3 Drawing Figures

FIG. 3

CONDUCTIVITY MONITORING SYSTEM

BACKGROUND OF THE INVENTION

This invention relates to an improved conductivity monitoring system or arrangement for monitoring the conductivity of a fluid flowing into and through a conductivity cell.

In blood dialysis, blood is passed through a dialysis unit on one side of a membrane of cellulose or the like, and dialysis solution is passed across the other side of the membrane, containing a sufficient concentration of salt to render the dialysis solution generally isotonic with respect to the blood. During dialysis, unwanted material such as urea, creatinine, and some water pass through the membrane from the blood into the dialysis solution, so that the dialyzer serves the function of the natural kidney in many important ways.

There are many different designs of apparatus for supplying the dialysis solution to the dialysis unit. One well known design is the RSP Dialyzer sold by Travenol Laboratories, Inc., of Deerfield, Illinois. Other dialysis delivery systems which are available provide a lower quantity of dialysis solution to a Kiil-type, flat plate dialyzer or the like, in which the dialysis solution typically passes through a dialyzer in a single path, then is discarded. In the copending applications of Willian J. Schnell and Ludwig Wolf, Jr., Ser. No. 519,731, filed Oct. 31, 1974, entitled "Swirling Flow Bubble Trap", and of Wendel V. Ebling, Rene G. Lamadrid and Earl G. Phillips, Ser. No. 519,730, filed Oct. 31, 1974, entitled "Device for Separating Low Density Materials Such as Gas Bubbles from a Liquid, and the Use Thereof in a Dialysis Delivery System" various improvements for dialysis systems also are disclosed.

The conductivity monitoring system of the present invention is particularly applicable for use with the improvements and in the dialysis systems disclosed in these two copending applications, as well as in other types of dialysis systems. Further still, the conductivity monitoring system is applicable for use in various other applications, for monitoring the conductivity of a fluid.

More particularly, the conductivity monitoring system of the invention includes at least three electrodes which are disposed with the housing of the conductivity cell, into and through which the fluid to be monitored is caused to flow. One of the electrodes is a common electrode and is positioned closer to one of the other two electrodes. The electrodes are energized by means of an oscillator which, in the illustrated embodiment, has an output frequency of 500 Hz. The output of the oscillator is coupled to the electrodes through a transformer. The common electrode is coupled to one terminal of the secondary of this transformer and the other two electrodes are coupled to its other terminal. Resistance means are connected in series with the respective ones of these two electrodes, and effectively function as constant current sources when the electrodes are energized. The conductivity is measured between the wide-spaced pair of electrodes, i.e, the common electrode and one of the other electrodes, and between the closer-spaced pair of electrodes, i.e., the common electrode and the other one of the two electrodes, and the difference is taken as the actual conductivity. With this arrangement, changes in the conductivity as a result of foreign matter collecting on the electrodes and the housing over a period of time are compensated for, since the difference in the conductivity between the two pairs of electrodes remain the same, even though the conductivity between each respective pair may change.

The primary winding of a second transformer is connected across the resistance means connected with the respective electrodes and provides a difference voltage at its secondary winding which represents the difference in the conductivity between the two pairs of electrodes. This difference voltage, after being amplified, is sampled with a phase sensitive sampled and hold circuit, and the sampled signal is coupled to indicator means to provide an indication of the value of the conductivity of the fluid and/or to activate a high level or a low level value of conductivity alarm.

Temperature sensing means also are provided for sensing the temperature of the fluid, and the output signal thereof is utilized to provide a temperature compensated conductivity signal. Detection means also are provided for detecting and indicating the failure or inoperability of the temperature sensing means.

The transformers, in addition, provide isolation between the conductivity signal and the electronics of the system.

Accordingly, it is an object of the present invention to provide an improved conductivity monitoring system or arrangement for monitoring the conductivity of a fluid flowing into and through a conductivity cell.

Other objects and features of the invention will be apparent from the description below.

DESCRIPTION OF THE PREFERRED EMBODIMENT

Figure 1:
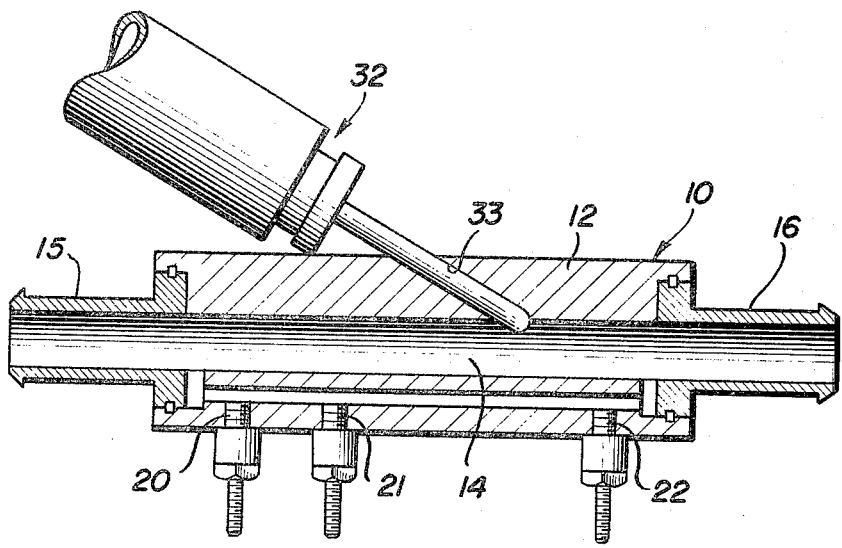
FIG. 1 is a sectional view of a conductivity cell assembly.

Referring now to the drawings, in FIG. 1, there is illustrated a conductivity cell assembly 10 exemplary of such an assembly which can be used in conjunction with or as part of the conductivity monitoring system of the present invention. The assembly 10 includes a housing 12 which may be cylindrical in cross section and which is of a non-conductive material such as plastic or the like. The housing 12 has a passage 14 extending through it, and end tubes 15 and 16 which may be adhesively or otherwise affixed with the housing to provide terminals to which hoses (not shown) may be attached for coupling a fluid into and through the housing.

Figure 2:
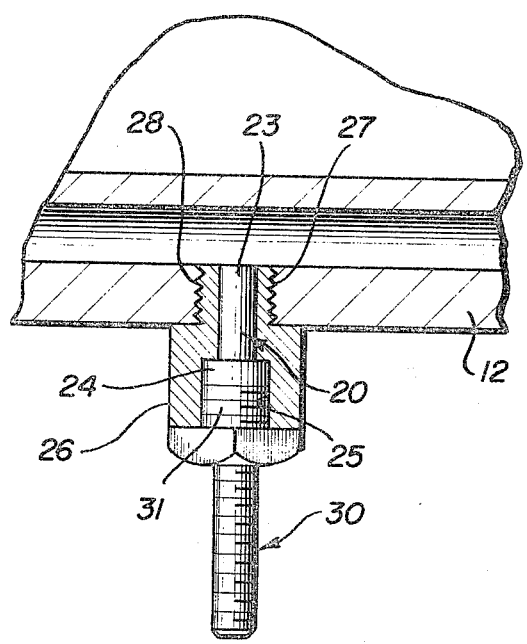
FIG. 2 is an enlarged, partial sectional view of an electrode assembly.

Three electrodes, 20, 21 and 22 are affixed to the housing 12, so as to extend into the passage 14 in contact with the fluid flowing through the housing. These electrodes 20–22 may be of any suitable electrically conducted material. In the illustrated embodiment, for example, these electrodes 20–22, as can be best seen in FIG. 2, each comprises a carbon electrode in the form of a cylindrical shaft 23 having an enlarged diameter head 24. The carbon electrode is disposed with a cavity 25 within a connector 26 which is of a non-conductive material and which has a threaded end 27 that is adapted to be threadedly received within a correspondingly threaded aperture 28 in the housing 12. The carbon electrode extends through the connector 26 into the passage 14 in the housing 12, so that the fluid flowing into and through the housing contacts it. A terminal 30 having a threaded end 31 is threaded into the cavity 25 in the connector 26 to establish electrical contact with the carbon electrode.

As can be best seen in FIG. 1, the electrode 21 is positioned closer to the electrode 20 than it is to the electrode 22. As described more fully below, the electrode 21 is utilized as a common electrode, for purposes which will be apparent from the description below.

Preferably and advantageously, the conductivity cell 10 also has a temperature sensing device 32 associated with it for sensing the temperature of the fluid flowing through the passage 14 in the housing 12. In the illustrated embodiment, the temperature sensing device 32 is a thermister which is extended through an aperture 33 in the housing 12, so that its end is disposed within the passage 14 in contact with the fluid flowing through the conductivity cell 10.

As indicated above, the conductivity cell assembly 10 together with the conductivity monitoring system of the present invention (described more fully below) may be utilized in a dialysis system as disclosed in the above-mentioned copending applications, for monitoring the conductivity of the dialysis solution which is caused to flow into and through the passage 14 in the housing 12. The applications for the conductivity monitoring system, however, is not limited to use in such dialysis systems, but may be utilized to monitor the conductivity of other fluids and other applications.

Figure 3:
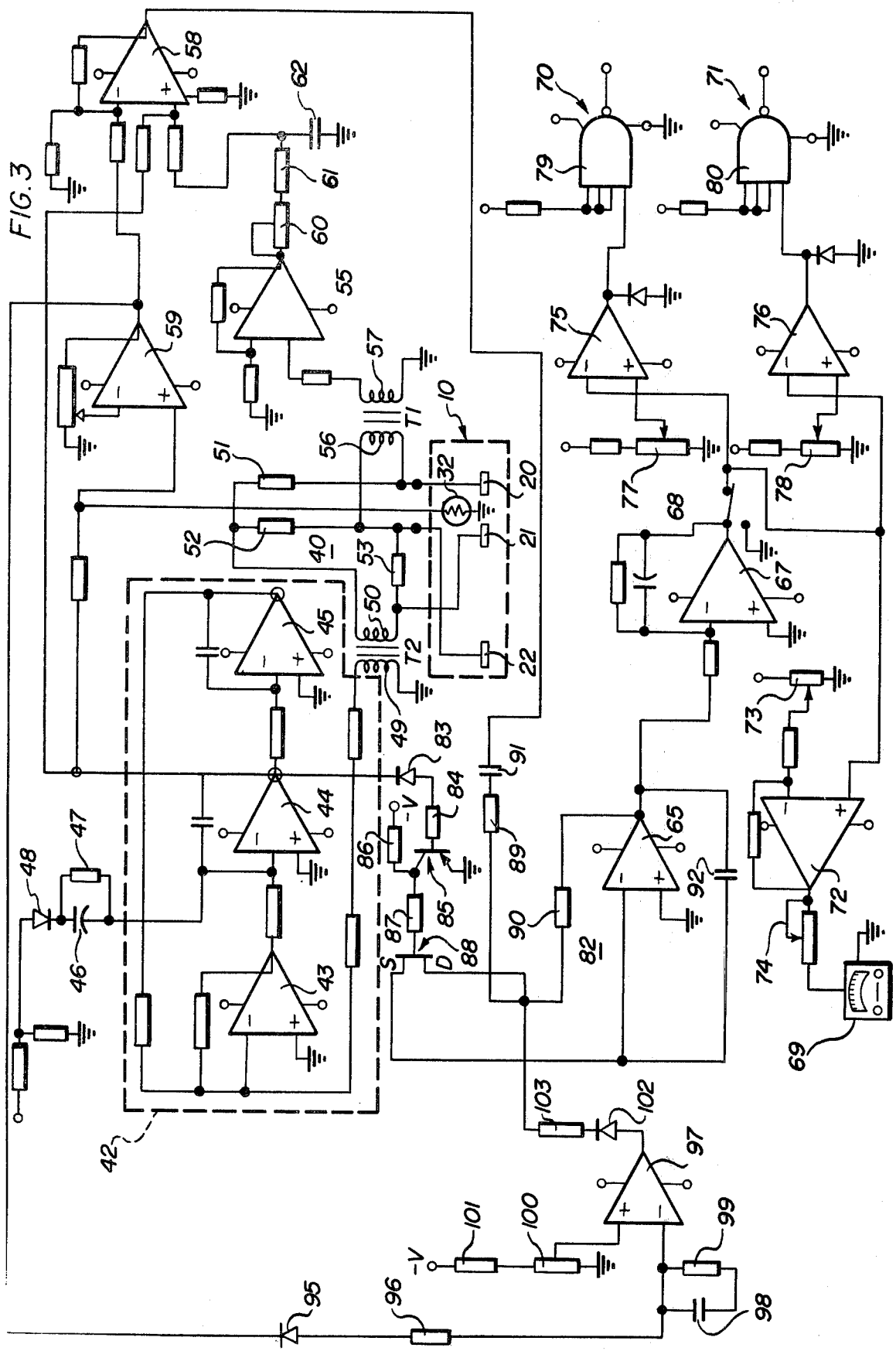
FIG. 3 is an electrical block diagram schematic of a conductivity monitoring system.

Referring now to FIG. 3, a conductivity cell 10 which may be of the above-described type is illustrated by means of the dash lined rectangle. The electrodes 20, 21 and 22 are illustrated as disposed within the conductivity cell 10, with the electrode 21 being a common electrode and positioned closer to the electrode 20 than to the electrode 22.

The electrodes 20-22 are coupled to a differencing and isolation circuit, generally indicated by the reference numeral 40, for monitoring and detecting the conductivity of the fluid flowing into and through the conductivity cell 10. Generally, in operation, the conductivity is measured between the wide-spaced pair of electrodes 21 and 22, and between the close-spaced pair of electrodes 20 and 21, with the difference being taken as the actual conductivity of the fluid. With this arrangement, the effect on the conductivity reading resulting from any foreign matter collected on the electrodes 20-21 over a period of time can be compensated for, since the conductivity between the respective pairs of electrodes may change, however, the difference between the conductivity of each of these pairs of electrodes will remain the same. Accordingly, these conductivity changes can be mathematically eliminated from the effect on the resulting conductivity reading.

More particularly, the input to the differencing and isolation circuit 40 is an oscillator 42 which can be of conventional design and which, in the illustrated embodiment, has an output frequency of 500 Hz., although its frequency is not critical except that other circuit parameters must be correspondingly adjusted to function with its set or established frequency. While the oscillator 42 can be of conventional design, in the illustrated embodiment, it is constructed of three operational amplifiers 43–45, each of which may be of the $\mu$A741 type coupled together to form a quadratic oscillator. Power is coupled to the oscillator 42 from a suitable source (not shown), and a start circuit consisting of a capacitor 46, a resistor 47 and a diode 48 is coupled between the source and the amplifier 44 to help guarantee the start of the oscillator 42 when power is initially turned on.

The output of the oscillator 42 is coupled to the differencing and isolating circuit 40, to the electrodes 20–22 thereof, by means of the primary winding 49 of a transformer T2. The secondary winding 50 of the transformer T2 has one terminal thereof coupled to the common electrode 21 and its other terminal coupled to the respective electrodes 20 and 22, via the resistors 51 and 52, respectively. A resistor 53 provides a high impedance path between the terminal connected to the common electrode 21 and the electrode 22. The two resistors 51 and 52 which, in the illustrated embodiment are 30 K ohm resistors, function as current sources for driving the electrodes 20-22, since these resistors 51 and 52 are on one side of the secondary winding 50 of the transformer T2 and drive approximately equal amounts of current to each of these two electrodes 20 and 22. Accordingly, with the constant current and a changing resistance due to changing conductivity in the fluid in the conductivity cell 10, a difference voltage which represents the difference in the conductivity between the electrodes 20 and 21 and the electrodes 21 and 22 is provided, and is coupled to the input of an amplifier 55.

This difference voltage is coupled to the amplifier 55, in the illustrated embodiment of the invention, by means of a transformer T1 which has its primary winding 56 coupled across the two resistors 51 and 52 such that the difference voltage is coupled through its secondary winding 57 to the input of the amplifier 55. Other arrangements for detecting and providing this difference voltage output also could be used. For example, two transformers or two operational amplifiers could be used, with each one thereof providing an output signal representative of the conductivity of its associated pair of electrodes. The output signals then could be summed by other suitable means such as, for example, another operational amplifier, to provide a difference voltage. An advantage of the described arrangement is that the transformers T1 and T2 also provide isolation of the conductivity signals from the electronics of the monitoring system, so that these conductivity signals are not adversely affected.

The output of the amplifier 55 is coupled to the input of another amplifier 58. In addition, an oscillator signal is taken from the amplifier 44 of the oscillator 42 and is coupled to the same input of the amplifier 58 for summing with the difference signal output amplifier 55. This oscillator signal functions to compensate for or eliminate any harmonic distortion which may result, to remove any such distortion from the output signal from the amplifier 58 which represents the value of the conductivity of the fluid in the conductivity cell 10.

The conductivity of the fluid within the conductivity cell 10 may fluctuate over a relatively wide range depending upon the temperature. Accordingly, as indicated above, a temperature sensing device 32 which, in the illustrated embodiment, is a thermistor, is installed in the conductivity cell 10 to sense the significant temperature changes in the fluid flowing into and through the conductivity cell. The signals from the temperature sensing device or thermistor 32 are coupled to the input of the amplifier 59, to provide a temperature compensated signal to the input of the amplifier 58. Since there is a phase shift in the difference voltage signal from the conductivity cell 10 and none from the thermistor 32, the difference voltage signal from the amplifier 55 is coupled through a phase shift network including the resistors 60 and 61 and the capacitor 62 so as to provide a phase corrected difference voltage signal to the input of the amplifier 58, which signal is summed with the temperature compensated signal from the amplifier 59. Accordingly, the output of the amplifier 58 is a temperature compensated conductivity signal which is phase corrected for the phase shift resulting from the cell 10 and the transformers T1 and T2.

This conductivity signal at the output of the amplifier 58 is an AC signal proportional in time to the temperature compensated conductivity signal. This AC conductivity signal is coupled to a sample and hold circuit 82 which may be of a conventional design employing an operational amplifier, such as the operational amplifier 65. In the illustrated embodiment, control of the sample and hold circuit 82 is exercised by the oscillator 42, with the output of the latter being coupled through a diode 83 and a resistor 84 to the base electrode of a PNP transistor 85. The collector electrode of the transistor 85 is coupled through a resistor 86 to a negative supply voltage, and further is coupled through a resistor 87 to the gate electrode of a field effect transistor (FET) 88. The source electrode of the FET 88 is coupled to the negative input of the operational amplifier 65, while its drain electrode is coupled to a common point between two resistors 89 and 90. The other terminal of the resistor 89 is coupled to a capacitor 91, while the other terminal of the resistor 90 is coupled to the output of the operational amplifier 65. A feedback coupling or hold capacitor 92 is coupled from the negative input to the output of the operational amplifier 65. The output of the amplifier 58 is coupled to the capacitor 91.

With the above-described arrangement of the sample and hold circuit 82, the operation is such that the circuit effectively "tracks" the output of the amplifier 58. More particularly, the oscillator 42 drives the transistor 85 to turn it ON and OFF. In the particular embodiment, the transistor 85 is turned ON only when the oscillator's negative output voltage exceeds 0.6 volts in absolute magnitude. When the transistor 85 turns ON, it, in turn, turns ON the FET 88. At this time, as with conventional sample and hold circuits, the operational amplifier 65 is tracking the input at its negative input, which input is the output of the amplifier 58. The capacitor 92 charges to a value corresponding to the output of the amplifier 58, which, of course, represents the conductivity of the fluid in the conductivity cell 10.

When the oscillator 42 again turns OFF the transistor 85, the FET 88 also turns OFF. In this state, the output of the operational amplifier 65 holds the voltage last sampled, since the capacitor 92 retains its charge, until the next sample period. In this fashion, the output voltage, or the signal representing the conductivity of the fluid in the conductivity cell 10, is continuously sampled, under the control of the oscillator 42. Therefore, the problem resulting from any phase shift in the signal output of the amplifier 58 is eliminated.

The sampled signals from the output of the operational amplifier 65 are coupled to the input of an amplifier 67 which is connected as an integrating amplifier. This amplifier 67 provides a DC signal which is proportional (average value) to the conductivity. The output of the amplifier 67 is coupled through a calibration switch 68, and is ultimately coupled to a meter 69 and to each of a high and low conductivity alarm 70 and 71.

More particularly, the output of the amplifier 67 is fed through the calibration switch 68 to the positive input of an operational amplifier 72. The other or minus input of the operational amplifier 72 has a DC reference point signal coupled to it which is adjusted by a potentiometer 73 to represent a zero current portion of the meter 69. A variable resistor 74 between the output of the amplifier 72 and the meter 69 is used to set the full scale adjustment of the meter 69. More specifically, at the output of the operational amplifier 72, the signal is adjusted to zero volts by adjusting the potentiometer 73 on the input of the amplifier 72. This accomplishes a setting of zero on the meter 69 independent of the full scale adjustment. The full scale adjustment then is provided by the variable resistor 74 between the output of the amplifier 72 and the meter 69. In practice, the zero current actually represents minus ten percent (−10%) of the meter scale, but it also represents zero current through the meter. The resistor 53 connected between the electrodes 21 and 22 is used to bias the conductivity cell 10 such that it will read negatively when no fluid is in the conductivity cell. In other words, when the conductivity cell is dry, the conductivity cell will read off the scale in the minus percentage region of the meter. The resistor 53 is of high enough value so as not to impact the calibration of the meter.

The output of the amplifier 67 also is fed through the calibration switch 68 to the negative inputs of each of the two operational amplifiers 75 and 76, each of which is connected as a comparator, the comparating voltages are coupled to the positive inputs of the respective amplifiers and are preset to specific values of conductivity, by means of the potentiometers 77 and 78, respectively. The outputs of the operational amplifiers 75 and 76 are coupled to the output gates 79 and 80, respectively. These gates 79 and 80 may be type 7413 Schmitt triggers which are triggered to provide an output signal for activating an alarm in the event that the value of conductivity of the fluid in the conductivity cell 10 is greater than or less than the high and low conductivity values established by the comparators 75 and 76. In a particular application, the comparing voltages of the comparators 75 and 76 are preset corresponding to a value of plus or minus five percent (5%) of a specific value of conductivity, so that the signals at the outputs of the gates 70 and 71 represent a logical signal which changes in logical value at plus and minus five percent respectively.

In the illustrated embodiment of the conductivity monitoring system, each of the amplifiers may be a type μA741 operational amplifier or one half of a type 5558 dual operational amplifier. In each case, these operational amplifiers are connected to function as an oscillator, a summing amplifier, a comparator, a sample and hold circuit or an integrator, as generally described above to provide the desired functions.

Accordingly, from the above description, it can be seen that the conductivity monitoring system can be used to monitor the conductivity of any fluid, such as a dialysis solution, which is caused to flow into and through the conductivity cell 10. With the described arrangement of the electrodes 20–22 in the conductivity cell, the effect on the conductivity of the electrodes 20-21 as a result of foreign matter collecting on them and on the housing over a period of time can be easily compensated for, so that a more accurate conductivity reading can be provided. Also, utilizing the transformers T1 and T2 to couple an energizing signal to the electrodes 20–21 and to detect and to couple a difference voltage to the meter 69 and to the high and low conductivity level alarms 70 and 71 isolate the conductivity signals from the electronics of the system, so that the conductivity signals are not adversely affected. The value of the conductivity of the fluid flowing into and through the conductivity cell can be indicated on the meter 69 and/or utilized to activate a high or low level conductivity alarm system. In the above-illustrated embodiment, the secondary winding 57 of the transformer T2 advantageously may be tuned by means of a capacitor (not shown) to reduce any loading and to provide a phase shift correction to the difference voltage signal. In such a case, the phase shift network including the resistors 60 and 61 and the capacitor 62 on the output of the amplifier 55 can be eliminated.

In the illustrated embodiment, it has been found that an erroneous indication of the conductivity of the fluid in the conductivity cell 10 can or will result if the thermistor 32 is defective or open-circuited. In such a case, the full output voltage of the oscillator 42 is coupled as an output to the amplifier 59. The output of the latter then is a high voltage which, upon being coupled to the amplifier 58 ultimately produces an erroneous indication.

Accordingly, to warn an operator of the failure of the thermistor 32, the output of the amplifier 59 is coupled through a diode 95 and a resistor 96 to the negative input of an operational amplifier 97. A filter network comprising a capacitor 98 and a resistor 99 also is coupled to the negative input of the operational amplifier 97 to filter the peak values. The positive input of the operational amplifier 97 is coupled to the tap on the variable resistor or potentiometer 100 which is connected in series with another resistor 101, between ground and a negative supply voltage. The output of the operational amplifier 97 is adjusted to go positive when the fluid temperature drops below approximately 25°C.

The output of the operational amplifier 97 is coupled through a diode 102 and a resistor 103 to the common point between the two resistors 89 and 90 of the sample and hold circuit 82.

In operation, the high reading, i.e., the high voltage at the output of the amplifier 59 as a result of the failure or open circuit condition of the thermistor 32, is sensed by the operational amplifier 97. The output of the latter in following the high voltage at its input goes negative and, upon being coupled to the sample and hold circuit 82, effectively overrides the signal output from the amplifier 58. The imposed output from the operational amplifier 97 causes the output of the operational amplifier 65 to trigger a warning alarm, in the manner more fully described above, when this output is coupled to the operational amplifier 67.

It will thus be seen that the objects set forth above, among those made apparent from the preceding description, are efficiently attained and certain changes may be made in the above construction. Accordingly, it is intended that all matter contained in the above description or shown in the accompanying drawings shall be interpreted as illustrative and not in a limiting sense.

What is claimed is:

1. In a conductivity monitoring system for monitoring the conductivity of a fluid flowing into and through a conductivity cell including electrode means within the conductivity cell for providing an output signal representative of the conductivity of said fluid, temperature sensing means disposed within said conductivity cell for providing an output signal representative of the temperature of said fluid flowing into and through said conductivity cell, indicator means, coupling means including summing means responsive to said output signals from said electrode means and said temperature sensing means to provide a temperature compensated conductivity output signal to said indicator means, the improvement comprising an arrangement for indicating a failure of said temperature sensing means, said arrangement comprising voltage sensing means for sensing the input to said summing means from said temperature sensing means, said voltage sensing means being responsive to the detection of a pre-established signal level and being operable to superimpose a signal on said output signal to said indicator means to operate the latter such that an indication of failure of said temperature sensing device is provided.

2. In a conductivity monitoring system, the improvement of claim 1, wherein said voltage sensing means comprises an operational amplifier.

* * * * *